(12) United States Patent
Pustovit

(10) Patent No.: US 9,254,381 B1
(45) Date of Patent: Feb. 9, 2016

(54) DEVICE, METHOD AND APPLICATION SOFTWARE FOR CURING OF BODY AILMENTS USING LOW-LEVEL ELECTRICAL CURRENT WAVEFORMS

(71) Applicant: Scientific Production Association Information Cell Biophysics, Moscow (RU)

(72) Inventor: Vladislav Pustovit, Moscow (RU)

(73) Assignee: Scientific Production Association Information Cell Biophysics, Moscow (RU)

( * ) Notice: Subject to any disclaimer, the term of this patent is extended or adjusted under 35 U.S.C. 154(b) by 0 days.

(21) Appl. No.: 14/520,725

(22) Filed: Oct. 22, 2014

(51) Int. Cl.
*A61N 1/36* (2006.01)
*A61N 1/32* (2006.01)

(52) U.S. Cl.
CPC ...................................... *A61N 1/326* (2013.01)

(58) Field of Classification Search
None
See application file for complete search history.

(56) References Cited

U.S. PATENT DOCUMENTS

| 2002/0032471 | A1* | 3/2002 | Loftin ................ A61N 1/37211 607/61 |
| 2012/0218498 | A1* | 8/2012 | Bonora et al. ................ 349/113 |
| 2013/0253613 | A1* | 9/2013 | Salahovic et al. ............... 607/61 |
| 2013/0303828 | A1* | 11/2013 | Hargrove ........... A61N 1/36014 600/13 |
| 2014/0049851 | A1* | 2/2014 | Snell et al. .................... 359/871 |
| 2014/0330336 | A1* | 11/2014 | Errico et al. ................... 607/45 |

\* cited by examiner

*Primary Examiner* — Erica Lee
(74) *Attorney, Agent, or Firm* — Bardmesser Law Group

(57) ABSTRACT

A method for changing clusterization pattern of water molecules in the human body in order to speed up the healing process. A mobile device has an application, which generates different audio streams based on a type of illness needed to be cured. A user selects the illness type on the mobile device screen and a special connector placed into an audio output port of the module device provides the electric carrier wave signal to a surface of a human body. A mobile device обязательно needs to be plugged into a power source in order to have enough power to generate the signal of required intensity. The electric signal penetrates into the human body upon contact with the connector and gradually changes the pattern of clusterization of the water molecules of a person to a normal (healthy) pattern.

9 Claims, 9 Drawing Sheets

A-A

B

DEVICE, METHOD AND APPLICATION SOFTWARE FOR CURING OF BODY AILMENTS USING LOW-LEVEL ELECTRICAL CURRENT WAVEFORMS

BACKGROUND OF THE INVENTION

1. Field of the Invention

This invention relates to a method and system for curing human body ailments through affecting clusterization of water molecules in human body by an electric signal generated by a mobile device, in order to assist in a healing process.

2. Description of the Related Art

Most of the cells of the human body consist of molecules of water. The adult male human body is approximately 65% water, and water is 11% hydrogen by mass but 67% by count of atoms (i.e., 67 atomic percent). The water molecules typically float freely when the water is in its normal liquid state. However, most water molecules in a human body are in cells, and such a state permits clusterization of water molecules.

However, as the research shows, once the person contracts a viral or bacterial illness or has some inflammation or other sort of health problems, the normal clusterization pattern changes. The research shows, that in order for a person to return to his or her healthy state, the clusterization pattern of water molecules needs to return to a normal healthy pattern. Presently, there are no systems that can affect clusterization of the water molecules in the human body in order to speed up the healing process.

Accordingly, a method and system for effective changing of the clusterization of the water molecules in the human body in order to assist in healing is desired.

SUMMARY OF THE INVENTION

Accordingly, the present invention is related to affecting clusterization of water molecules in human body by using an electric signal generated by a mobile device in order to assist in a healing process that substantially obviates one or more of the disadvantages of the related art.

The present invention is directed to a method for changing clusterization pattern of water molecules in the human body in order to speed up the healing process. A mobile device has an application, which generates different audio streams based on a type of illness, which needs to be cured. A user selects the illness type on the mobile device screen and a special connector placed into an audio output port of the module device provides the electric carrier wave signal in human body. A mobile device normally needs to be plugged into a power source (e.g., a wall outlet) to receive the carrier signal and sufficient current to drive the connector, see FIG. 3. The electric current of about 1 mA and about 1-1.5 V rms flows into the human body upon contact with the connector and gradually changes the pattern of clusterization of the water molecules of a person to a normal (healthy) pattern.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED FIGURES

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE PREFERRED EMBODIMENTS

Figure 1A:
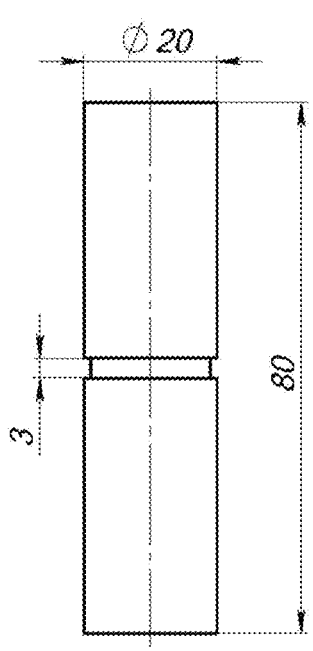
FIGS. 1A-1D illustrate a connector used in the exemplary embodiment.

Reference will now be made in detail to the preferred embodiments of the present invention, examples of which are illustrated in the accompanying drawings.

The present invention is directed to a method for changing clusterization patterns of water molecules in the human body in order to accelerate the healing process. A surprising and unexpected phenomenon discovered by the inventor is that water clusters in the human body act as memory elements, and can be repaired by using current of specific parameters. Water clustering is one of the more puzzling properties of water. It has been discovered that water molecules form an infinite hydrogen-bonded network with localized and structured clustering. The middling strength of the connecting hydrogen bonds seems ideally suited to life processes, being easily formed but not too difficult to break. Liquid water is not homogeneous at the nanoscopic level. Small clusters of four water molecules may come together to form water bicyclo-octamers. Bicyclo-octamers may cluster further, with only themselves, to form highly symmetric 280-molecule icosahedral water clusters that are able to interlink and tessellate throughout space. A mixture of water cyclic pentamers and tricyclo-decamers can bring about the same resultant clustering.

A fluctuating self-replicating network of water molecules, with localized and overlapping icosahedral symmetry, was first proposed to exist in liquid water in 1998 and the structure subsequently independently found, by X-ray diffraction, in water nanodrops in 2001. The clusters formed can interconvert between lower and higher density forms by bending, but not breaking, some of the hydrogen bonds. Structuring may also flicker between statistically and topographically equivalent clusters but involving different molecules by shifting their cluster centers. As the temperature increases the average cluster size, the cluster integrity and the proportion in the low-density form all decrease.

According to the exemplary embodiment, a mobile device has an application, which generates different audio stream signals at the audio jack based on a type of illness, which needs to be cured, by utilizing clusterization properties of water in the human body. A user selects the illness type on the mobile device screen and a special connector placed into an audio output port of the module device provides the electric current having a particular waveform (e.g., 50 or 60 Hz carrier frequency, +/−10%, with a high frequency component added) to a surface of a human body. A mobile device needs to be plugged into a power source in order to have enough power to generate the required current and overcome the skin resistance. The electric current into the human body upon contact with the connector and gradually changes the pattern of clusterization of the water molecules of a person to a normal (healthy) pattern, thereby curing such diseases as respiratory diseases, herpes virus, staphylococcal infections and so on.

Figure 1D:
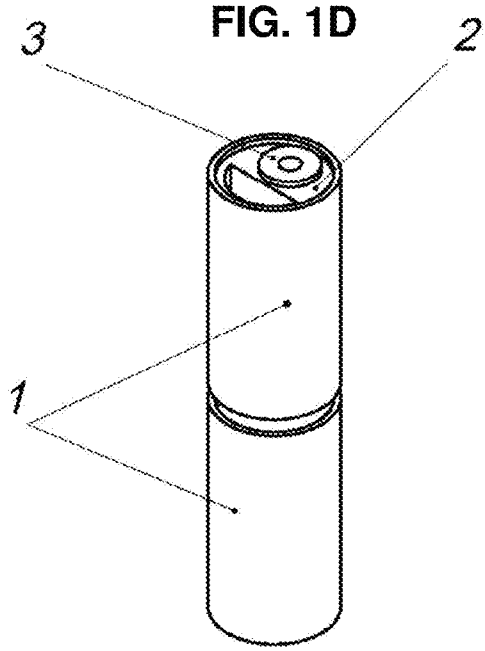
Figure 1B:
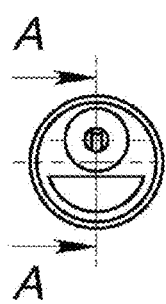
Figure 1C:
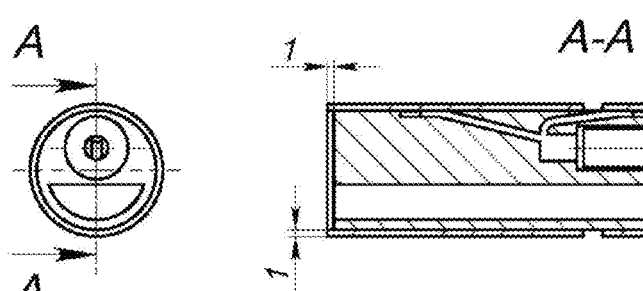

FIGS. 1A-1D illustrate a connector used in the exemplary embodiment. FIG. 1A shows a side view, FIG. 1B shows an edge-on view, FIG. 1C shows a cross-sectional view along A-A, and FIG. 1D shows a 3-dimensional isometric view. The dimensions, in mm, are exemplary. The exemplary embodiment uses a cylindrical connector adapted for connection to an audio output of a mobile device. However, a connector of an arbitrary shape can be used (e.g., oval, flat, cylindrical, even the back surface of the smartphone can be used as a conductive surface to the skin) as long as it uses a standard cable for connecting to the standard audio output of a mobile device. The connector provides a required contact area with the skin of a human body, preferably at least 5 $cm^2$ of contact area. The back surface of the smartphone, for example, can be connected directed to the DAC of the smartphone.

Figure 2A:
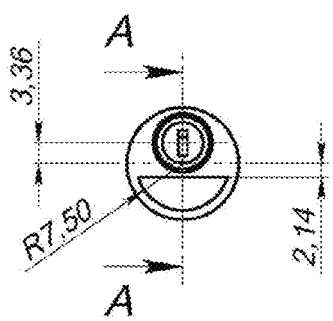
FIGS. 2A-2D illustrate additional views of the connector with the exemplary dimensions used in the exemplary embodiment.
Figure 2B:
Figure 2C:
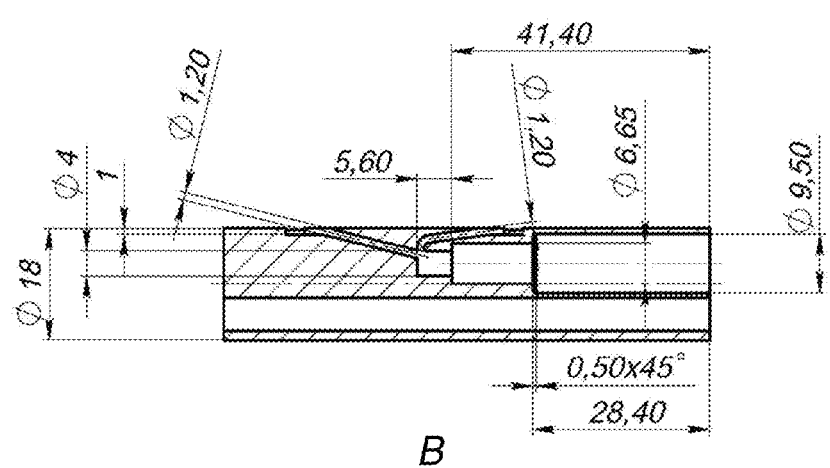
Figure 2D:
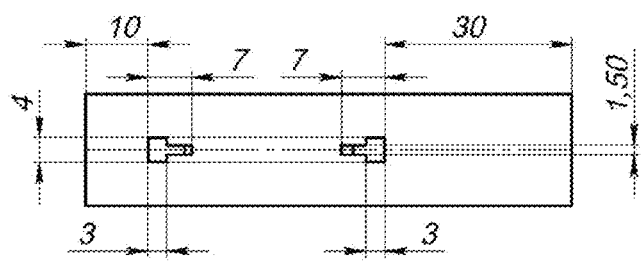

FIGS. 2A-2D illustrate additional views of the connector with the exemplary dimensions (in mm) used in the exemplary embodiment. FIG. 2A shows a side view, FIG. 2B shows a side view, FIG. 2C shows a cross-sectional view along A-A, and FIG. 2D shows another side view. According to the exemplary embodiment, the connector is attached to an audio output of the mobile device. A user launches a healing application on the mobile device and selects a type of illness that needs to be cured. The application begins playing out an audio file that produces an electric signal which, in turn, results in corresponding current flowing into the human body. The signal is approximately 3 seconds long and is played repeatedly (in a loop).

The electric waveform produced by the digital signal is received by the connector and passed on to a body of a person via direct skin contact. The electric current produced by the audio jack and that flows into the human body through the connector is on order of 1 mA (+/−10%). The root mean square (RMS) voltage of the AC current is 1-1.5 V (+/−10%), and roughly 1.6-1.9 peak to peak voltage (+/−10%). The frequency of the carrier wave is 50 Hz (+/−10%) based on the European standard frequency, or 60 Hz (+/−10%) based on the US standard. The carrier wave has an additional high frequency signal produced by the mobile device that is added to it, and which is disease- or ailment-dependent.

Figure 3:
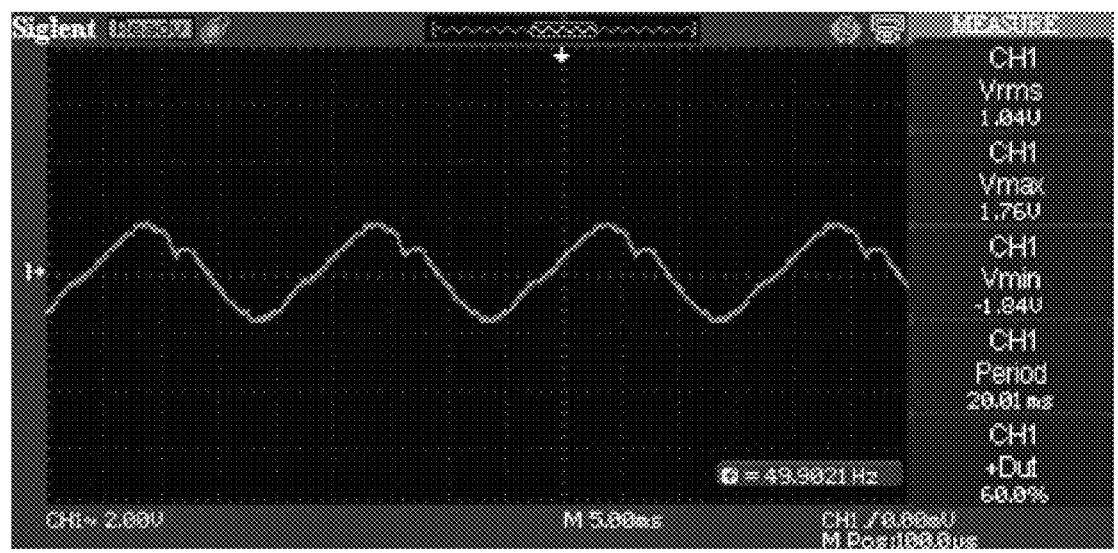
FIG. 3 shows a carrier waveform used in the present invention.

FIG. 3 shows a carrier waveform received through a standard power outlet, as used in the present invention.

Figure 4:
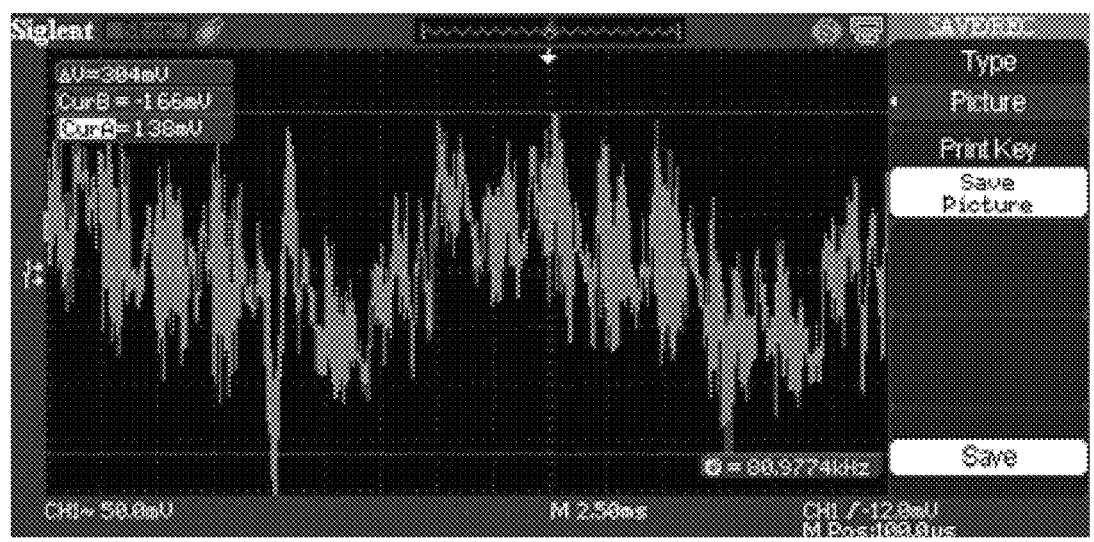
FIGS. 4-5 illustrate examples of signals produce by a mobile application for curing specific ailments.
Figure 5:
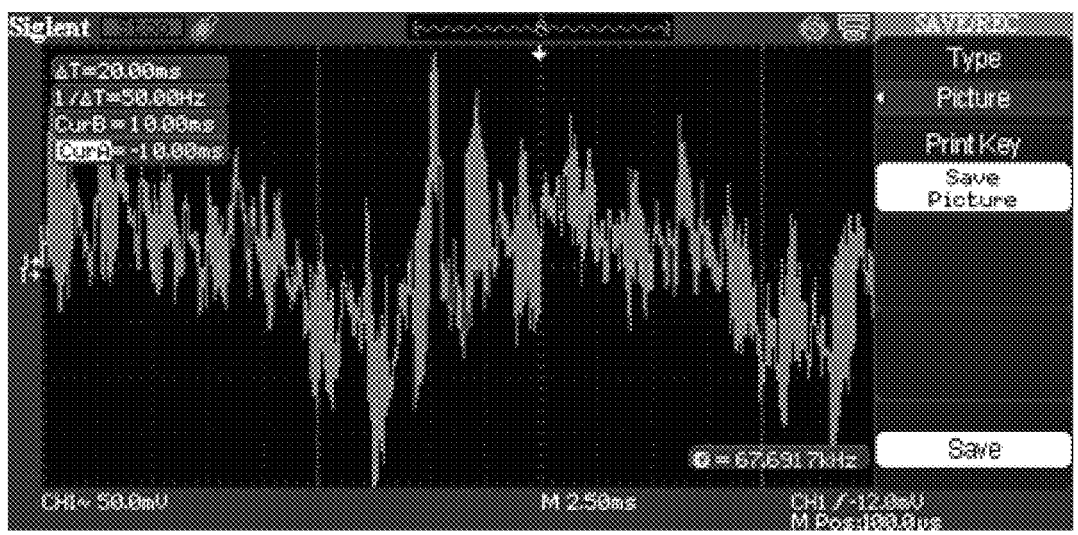

FIGS. 4-5 illustrate examples of waveforms produce by a mobile application. Each of these signals is intended for a particular illness. In this case, FIG. 4 is an alternating electric signal (i.e., carrier waveform modulated by an audio signal) for treating acute upper respiratory infection, and FIG. 5 is an alternating electric signal for treating angina. Other ailments are also treated by signals that are of a similar type to those shown in these figures. The application of such a type of signal produces an unexpected result of fast healing of a person due to changes in clusterization pattern of water molecules in a body (and the specific organs) of an affected person.

Using the approach described herein, the following ailments have been treated: dust allergy, pollen and plant allergy, allergy to animals, upper respiratory disease, herpes, nasal adenoids, nasal rhinitis, nasal sinusitis, angina, chronic angina, stomach flu/gastroenteritis, gastritis, gall bladder disease, pancreatic disorder, hepatitis, uterine infection, milk gland infection, candidotic infections, kidney infections, adenoviral infections, urinary bladder infections, prostate disorder, asthma, bronchitis, joint pain, lowered immunity, migraines, detoxification, nasopharingitis (rhinoviral infection), ovarian infection, thyroid gland disorder, adrenal gland disorder.

The signal that is sent to the connector, in essence, is formed of a carrier waveform (50 or 60 Hz) combined with a linear combination of other waveforms, typically at higher frequencies (up to 700 KHz). Each such waveform can be represented by an amplitude and frequency, i.e., if the final signal is represented as a sum of sinusoids, then what is necessary is to determine the frequency and amplitude (coefficient) of each sinusoid. The process of determining these requires generating a digital representation of medications that address specific ailments needs to be created. To do so, the following steps are performed:

1. in a water bidistillate, the medication is dissolved in proportion 70/30 water/medication, with water being at least 70%.

2. a wideband analog to digital converter is connected to the power supply (50/60 Hz, 220/110 V) in order to ensure the presence of the carrier on the sensing element of the ADC. The contact area of the ADC is preferably at least 5 $cm^2$.

3. the sensing element of the ADC is dipped in the water/medication liquid, and receives and records the signal from the sample, of a duration of about 3-7 seconds.

Figure 8:
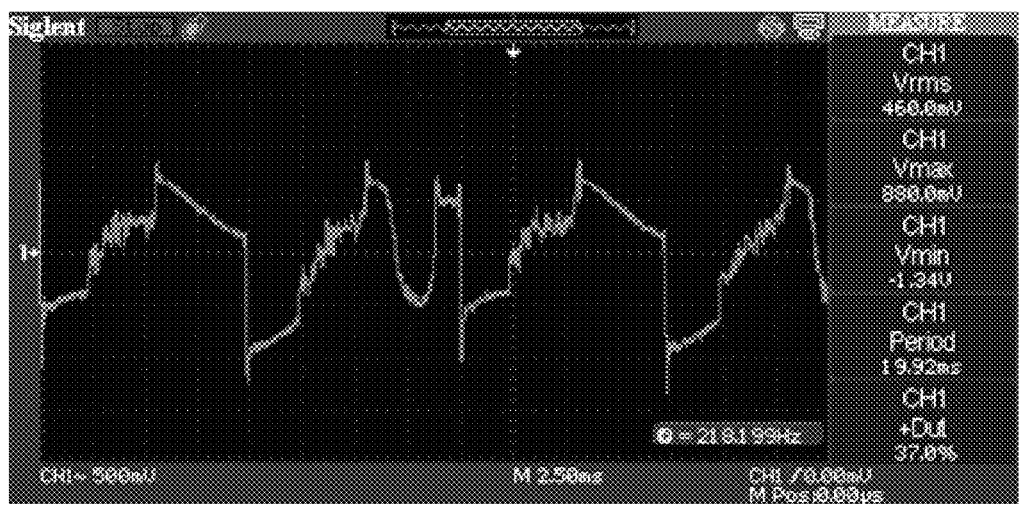
FIGS. 8-12 show exemplary waveforms that clusterize water for some of the medications that are available in Russia.
Figure 9:
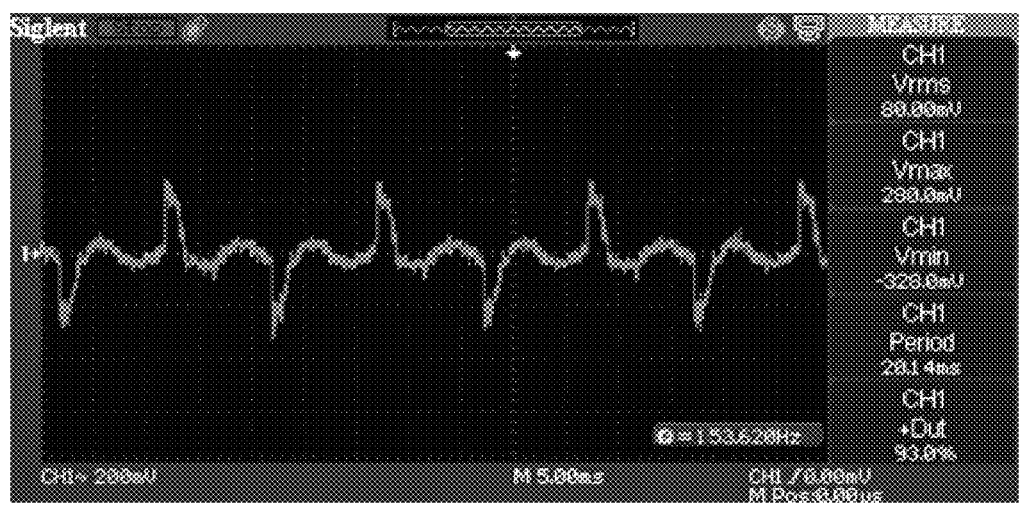
Figure 10:
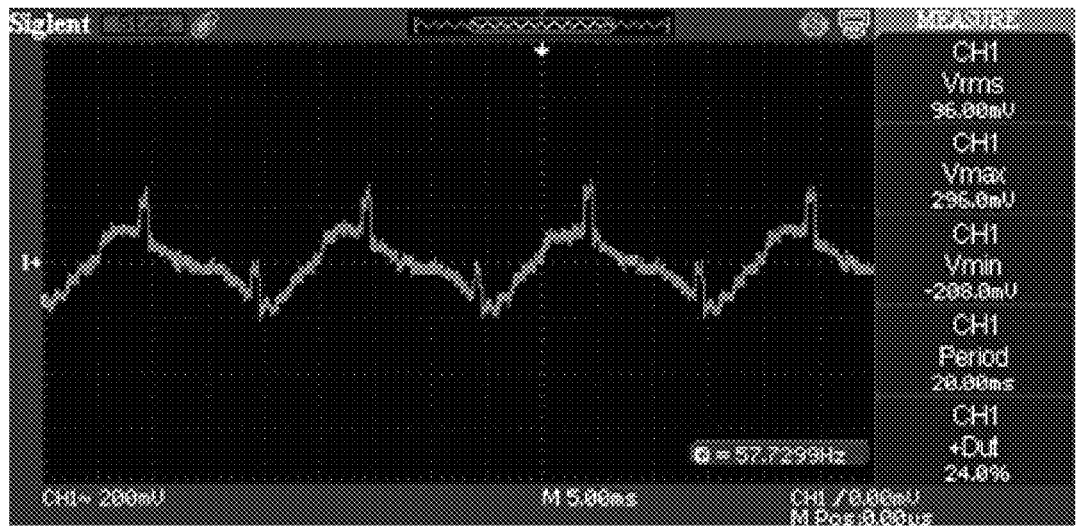
Figure 11:
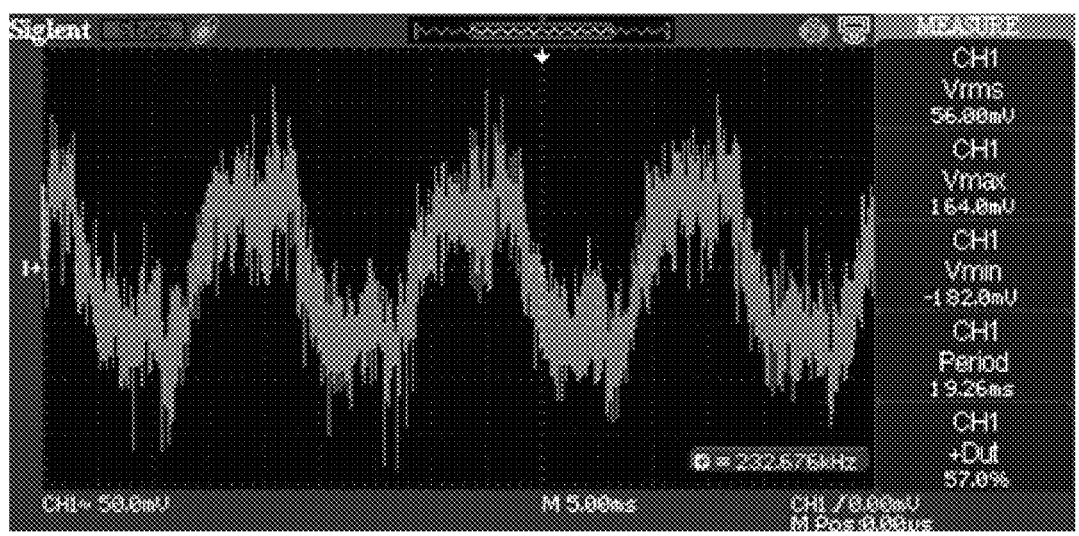
Figure 12:
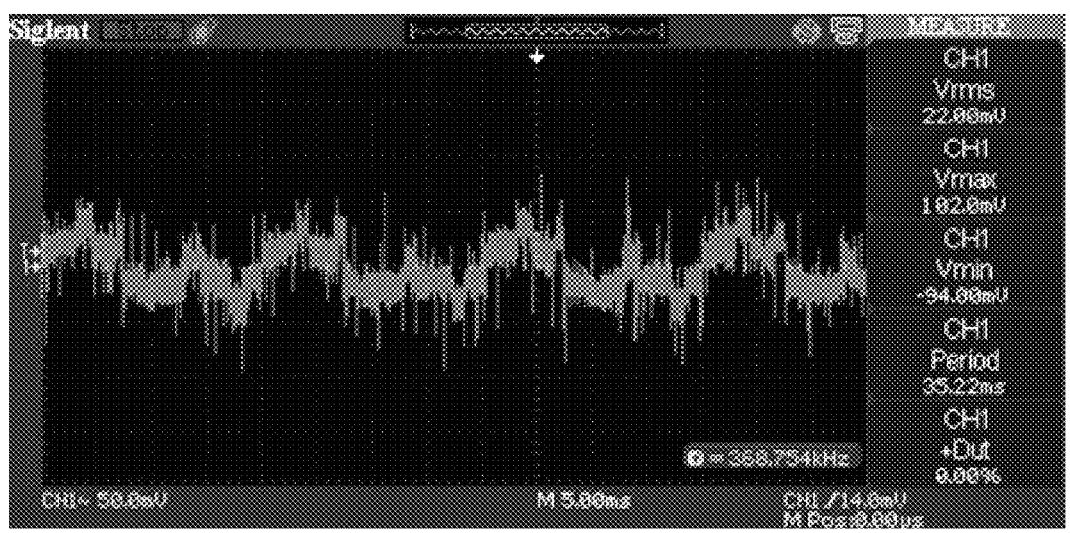

4. the carrier (50/60 Hz) is then filtered from the received signal, which is then identified with the particular medication. Examples for some of the medications that are available in Russia are shown in FIGS. 8-12, where FIG. 8 shows the alternating electric signal waveform for Amixin, FIG. 9 shows the alternating electric signal waveform for Cortexin, FIG. 10 shows the alternating electric signal waveform for Semax, FIG. 11 shows the alternating electric signal waveform for Vlairin, FIG. 12 shows the alternating electric signal waveform for Deltaran. A typical process for determining the appropriate signal for improving the immune system would be to determine the waveforms for various immune-enhancement drugs, and then try (in vivo) various signals that represent a linear superposition of the carrier waveform and the waveforms for the immune-enhancement drugs with different coefficients, to see which linear superposition delivers the best result.

5. to solve a specific health issue, a signal is required, which is typically a combination of multiple medication-specific waveforms generated using steps 1-4, depending on which medications are used for the particular disease or ailment. A final signal is compiled based on repetitive testing of various linear combinations of the medication-specific waveforms, and such a signal (roughly 3-7 seconds long) typically runs in a loop for about 10-30 minutes. Laboratory studies and in vitro studies are performed to determine the coefficients of the waveforms needed for the linear combination for the final signal.

6. the final signal (3-7 seconds) is added to the database, and can be used by the user to select using an application on his smartphone.

Figure 6:
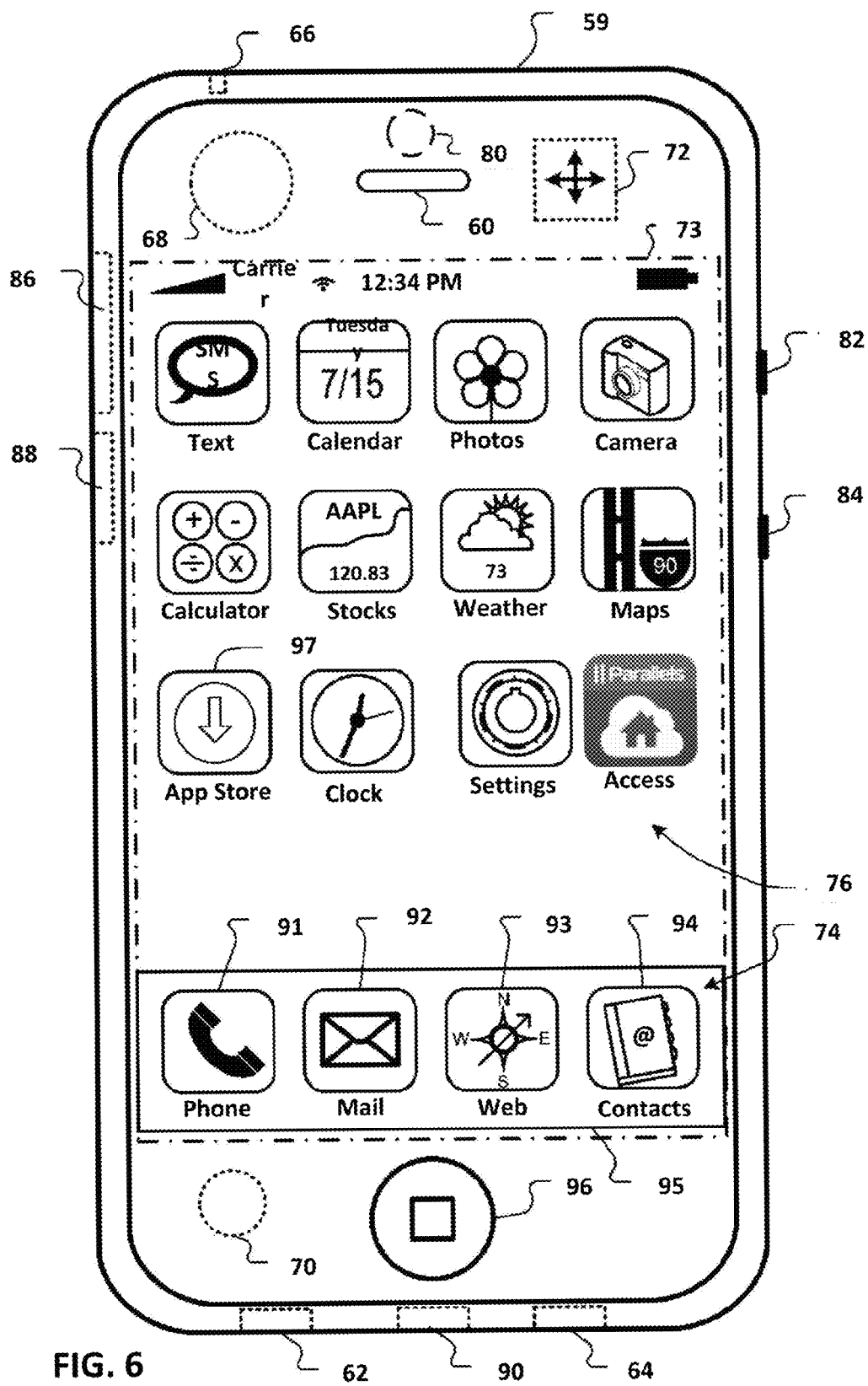
FIG. 6 is a block diagram of an exemplary mobile device that can be used in the invention.
Figure 7:
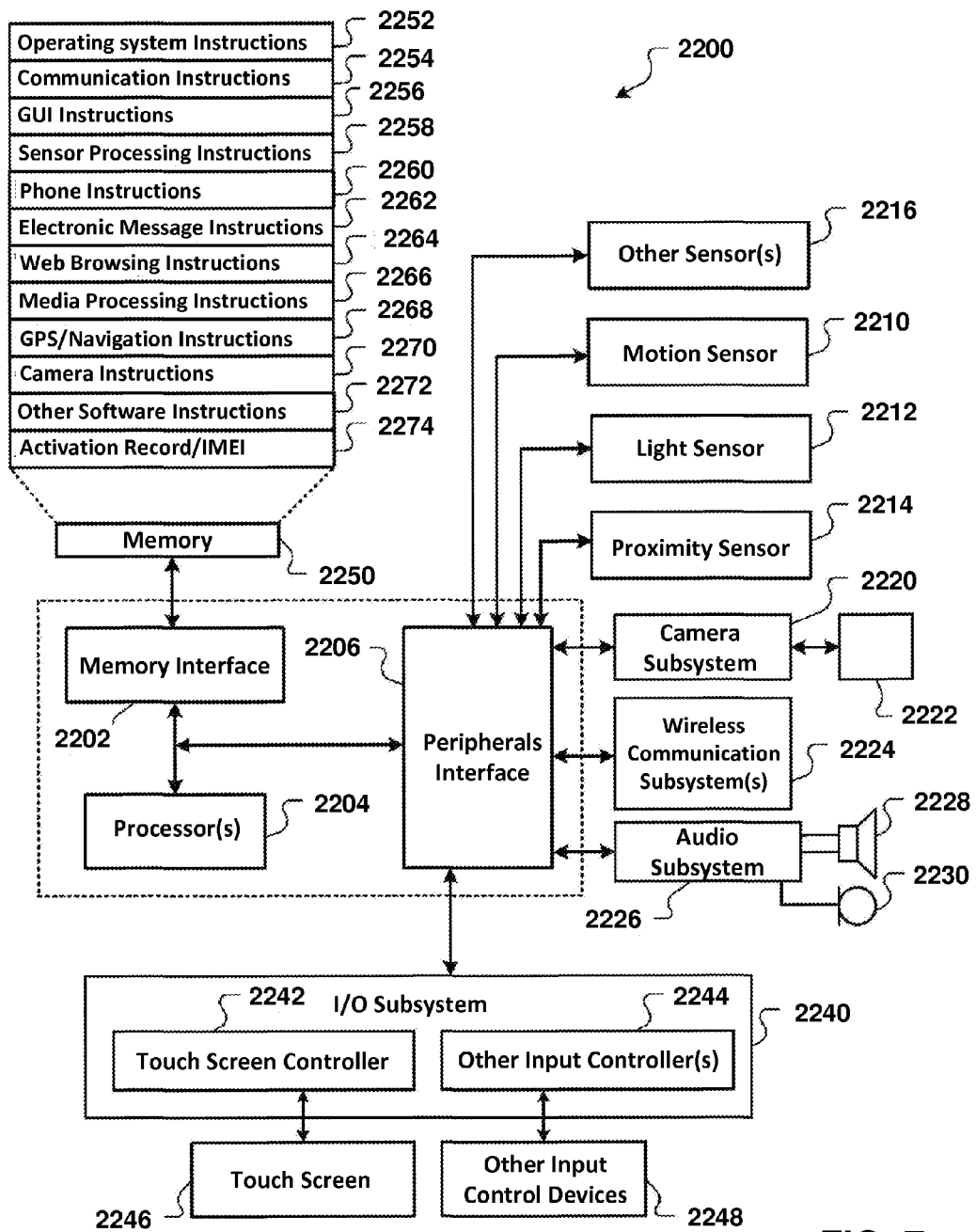
FIG. 7 is a block diagram of an exemplary implementation of the mobile device.

FIG. 6 is a block diagram of an exemplary mobile device 59 on which the invention can be implemented. The mobile device 59 can be, for example, a personal digital assistant, a cellular telephone, a network appliance, a camera, a smart phone, an enhanced general packet radio service (EGPRS) mobile phone, a network base station, a media player, a navigation device, an email device, a game console, or a combination of any two or more of these data processing devices or other data processing devices.

In some implementations, the mobile device 59 includes a touch-sensitive display 73. The touch-sensitive display 73 can implement liquid crystal display (LCD) technology, light emitting polymer display (LPD) technology, or some other display technology. The touch-sensitive display 73 can be sensitive to haptic and/or tactile contact with a user.

In some implementations, the touch-sensitive display 73 can comprise a multi-touch-sensitive display 73. A multi-touch-sensitive display 73 can, for example, process multiple simultaneous touch points, including processing data related to the pressure, degree and/or position of each touch point. Such processing facilitates gestures and interactions with multiple fingers, chording, and other interactions. Other touch-sensitive display technologies can also be used, e.g., a display in which contact is made using a stylus or other pointing device.

In some implementations, the mobile device 59 can display one or more graphical user interfaces on the touch-sensitive display 73 for providing the user access to various system objects and for conveying information to the user. In some implementations, the graphical user interface can include one or more display objects 74, 76. In the example shown, the display objects 74, 76, are graphic representations of system objects. Some examples of system objects include device functions, applications, windows, files, alerts, events, or other identifiable system objects.

In some implementations, the mobile device 59 can implement multiple device functionalities, such as a telephony device, as indicated by a phone object 91; an e-mail device, as indicated by the e-mail object 92; a network data communication device, as indicated by the Web object 93; a Wi-Fi base station device (not shown); and a media processing device, as indicated by the media player object 94.

In some implementations, particular display objects 74, e.g., the phone object 91, the e-mail object 92, the Web object 93, and the media player object 94, can be displayed in a menu bar 95. In some implementations, device functionalities can be accessed from a top-level graphical user interface, such as the graphical user interface illustrated in the figure. Touching one of the objects 91, 92, 93 or 94 can, for example, invoke corresponding functionality.

In some implementations, the mobile device 59 can implement network distribution functionality. For example, the functionality can enable the user to take the mobile device 59 and its associated network while traveling. In particular, the mobile device 59 can extend Internet access (e.g., Wi-Fi) to other wireless devices in the vicinity. For example, mobile device 59 can be configured as a base station for one or more devices. As such, mobile device 59 can grant or deny network access to other wireless devices.

In some implementations, upon invocation of device functionality, the graphical user interface of the mobile device 59 changes, or is augmented or replaced with another user interface or user interface elements, to facilitate user access to particular functions associated with the corresponding device functionality. For example, in response to a user touching the phone object 91, the graphical user interface of the touch-sensitive display 73 may present display objects related to various phone functions; likewise, touching of the email object 92 may cause the graphical user interface to present display objects related to various e-mail functions; touching the Web object 93 may cause the graphical user interface to present display objects related to various Web-surfing functions; and touching the media player object 94 may cause the graphical user interface to present display objects related to various media processing functions.

In some implementations, the top-level graphical user interface environment or state can be restored by pressing a button 96 located near the bottom of the mobile device 59. In some implementations, each corresponding device functionality may have corresponding "home" display objects displayed on the touch-sensitive display 73, and the graphical user interface environment can be restored by pressing the "home" display object.

In some implementations, the top-level graphical user interface can include additional display objects 76, such as a short messaging service (SMS) object, a calendar object, a photos object, a camera object, a calculator object, a stocks object, a weather object, a maps object, a notes object, a clock object, an address book object, a settings object, and an app store object 97. Touching the SMS display object can, for example, invoke an SMS messaging environment and supporting functionality; likewise, each selection of a display object can invoke a corresponding object environment and functionality.

Additional and/or different display objects can also be displayed in the graphical user interface. For example, if the device 59 is functioning as a base station for other devices, one or more "connection" objects may appear in the graphical user interface to indicate the connection. In some implementations, the display objects 76 can be configured by a user, e.g., a user may specify which display objects 76 are displayed, and/or may download additional applications or other software that provides other functionalities and corresponding display objects.

In some implementations, the mobile device 59 can include one or more input/output (I/O) devices and/or sensor devices. For example, a speaker 60 and a microphone 62 can be included to facilitate voice-enabled functionalities, such as phone and voice mail functions. In some implementations, an up/down button 84 for volume control of the speaker 60 and the microphone 62 can be included. The mobile device 59 can also include an on/off button 82 for a ring indicator of incoming phone calls. In some implementations, a loud speaker 64 can be included to facilitate hands-free voice functionalities, such as speaker phone functions. An audio jack 66 can also be included for use of headphones and/or a microphone.

In some implementations, a proximity sensor 68 can be included to facilitate the detection of the user positioning the mobile device 59 proximate to the user's ear and, in response, to disengage the touch-sensitive display 73 to prevent accidental function invocations. In some implementations, the touch-sensitive display 73 can be turned off to conserve additional power when the mobile device 59 is proximate to the user's ear.

Other sensors can also be used. For example, in some implementations, an ambient light sensor 70 can be utilized to facilitate adjusting the brightness of the touch-sensitive display 73. In some implementations, an accelerometer 72 can be utilized to detect movement of the mobile device 59, as indicated by the directional arrows. Accordingly, display objects and/or media can be presented according to a detected orientation, e.g., portrait or landscape.

In some implementations, the mobile device 59 may include circuitry and sensors for supporting a location determining capability, such as that provided by the global positioning system (GPS) or other positioning systems (e.g., systems using Wi-Fi access points, television signals, cellular grids, Uniform Resource Locators (URLs)). In some implementations, a positioning system (e.g., a GPS receiver) can be integrated into the mobile device 59 or provided as a separate device that can be coupled to the mobile device 59 through an interface (e.g., port device 90) to provide access to location-based services.

The mobile device 59 can also include a camera lens and sensor 80. In some implementations, the camera lens and sensor 80 can be located on the back surface of the mobile device 59. The camera can capture still images and/or video.

The mobile device 59 can also include one or more wireless communication subsystems, such as an 802.11b/g communication device 86, and/or a BLUETOOTH communication device 88. Other communication protocols can also be supported, including other 802.x communication protocols (e.g., WiMax, Wi-Fi, 3G, LTE), code division multiple access (CDMA), global system for mobile communications (GSM), Enhanced Data GSM Environment (EDGE), etc.

In some implementations, the port device 90, e.g., a Universal Serial Bus (USB) port, or a docking port, or some other wired port connection, is included. The port device 90 can, for example, be utilized to establish a wired connection to other computing devices, such as other communication devices 59, network access devices, a personal computer, a printer, or other processing devices capable of receiving and/or transmitting data. In some implementations, the port device 90 allows the mobile device 59 to synchronize with a host device using one or more protocols, such as, for example, the TCP/IP, HTTP, UDP and any other known protocol. In some implementations, a TCP/IP over USB protocol can be used.

FIG. 6 is a block diagram 2200 of an example implementation of the mobile device 59. The mobile device 59 can include a memory interface 2202, one or more data processors, image processors and/or central processing units 2204, and a peripherals interface 2206. The memory interface 2202, the one or more processors 2204 and/or the peripherals interface 2206 can be separate components or can be integrated in one or more integrated circuits. The various components in the mobile device 59 can be coupled by one or more communication buses or signal lines.

Sensors, devices and subsystems can be coupled to the peripherals interface 2206 to facilitate multiple functionalities. For example, a motion sensor 2210, a light sensor 2212, and a proximity sensor 2214 can be coupled to the peripherals interface 2206 to facilitate the orientation, lighting and proximity functions described above. Other sensors 2216 can also be connected to the peripherals interface 2206, such as a positioning system (e.g., GPS receiver), a temperature sensor, a biometric sensor, or other sensing device, to facilitate related functionalities.

A camera subsystem 2220 and an optical sensor 2222, e.g., a charged coupled device (CCD) or a complementary metal-oxide semiconductor (CMOS) optical sensor, can be utilized to facilitate camera functions, such as recording photographs and video clips.

Communication functions can be facilitated through one or more wireless communication subsystems 2224, which can include radio frequency receivers and transmitters and/or optical (e.g., infrared) receivers and transmitters. The specific design and implementation of the communication subsystem 2224 can depend on the communication network(s) over which the mobile device 59 is intended to operate. For example, a mobile device 59 may include communication subsystems 2224 designed to operate over a GSM network, a GPRS network, an EDGE network, a Wi-Fi or WiMax network, and a BLUETOOTH network. In particular, the wireless communication subsystems 2224 may include hosting protocols such that the device 59 may be configured as a base station for other wireless devices.

An audio subsystem 2226 can be coupled to a speaker 2228 and a microphone 2230 to facilitate voice-enabled functions, such as voice recognition, voice replication, digital recording, and telephony functions. The I/O subsystem 2240 can include a touch screen controller 2242 and/or other input controller(s) 2244. The touch-screen controller 2242 can be coupled to a touch screen 2246. The touch screen 2246 and touch screen controller 2242 can, for example, detect contact and movement or break thereof using any of multiple touch sensitivity technologies, including but not limited to capacitive, resistive, infrared, and surface acoustic wave technologies, as well as other proximity sensor arrays or other elements for determining one or more points of contact with the touch screen 2246.

The other input controller(s) 2244 can be coupled to other input/control devices 2248, such as one or more buttons, rocker switches, thumb-wheel, infrared port, USB port, and/or a pointer device such as a stylus. The one or more buttons (not shown) can include an up/down button for volume control of the speaker 2228 and/or the microphone 2230.

In one implementation, a pressing of the button for a first duration may disengage a lock of the touch screen 2246; and a pressing of the button for a second duration that is longer than the first duration may turn power to the mobile device 59 on or off. The user may be able to customize a functionality of one or more of the buttons. The touch screen 2246 can, for example, also be used to implement virtual or soft buttons and/or a keyboard.

In some implementations, the mobile device 59 can present recorded audio and/or video files, such as MP3, AAC, and MPEG files. In some implementations, the mobile device 59 can include the functionality of an MP3 player. The mobile device 59 may, therefore, include a 32-pin connector that is compatible with the MP3 player. Other input/output and control devices can also be used.

The memory interface 2202 can be coupled to memory 2250. The memory 2250 can include high-speed random access memory and/or non-volatile memory, such as one or more magnetic disk storage devices, one or more optical storage devices, and/or flash memory (e.g., NAND, NOR). The memory 2250 can store an operating system 2252, such as Darwin, RTXC, LINUX, UNIX, OS X, ANDROID, IOS, WINDOWS, or an embedded operating system such as VxWorks. The operating system 2252 may include instructions for handling basic system services and for performing hardware dependent tasks. In some implementations, the operating system 2252 can be a kernel (e.g., UNIX kernel).

The memory 2250 may also store communication instructions 2254 to facilitate communicating with one or more additional devices, one or more computers and/or one or more servers. The memory 2250 may include graphical user interface instructions 2256 to facilitate graphic user interface processing including presentation, navigation, and selection within an application store; sensor processing instructions 2258 to facilitate sensor-related processing and functions; phone instructions 2260 to facilitate phone-related processes and functions; electronic messaging instructions 2262 to facilitate electronic-messaging related processes and functions; web browsing instructions 2264 to facilitate web browsing-related processes and functions; media processing instructions 2266 to facilitate media processing-related processes and functions; GPS/Navigation instructions 2268 to facilitate GPS and navigation-related processes and instructions; camera instructions 2270 to facilitate camera-related processes and functions; and/or other software instructions 2272 to facilitate other processes and functions.

Each of the above identified instructions and applications can correspond to a set of instructions for performing one or more functions described above. These instructions need not be implemented as separate software programs, procedures or modules. The memory 2250 can include additional instructions or fewer instructions. Furthermore, various functions of the mobile device 59 may be implemented in hardware and/or in software, including in one or more signal processing and/or application specific integrated circuits.

Having thus described a preferred embodiment, it should be apparent to those skilled in the art that certain advantages of the described method and apparatus have been achieved.

It should also be appreciated that various modifications, adaptations, and alternative embodiments thereof may be made within the scope and spirit of the present invention. The invention is further defined by the following claims.

What is claimed is:

1. A method for changing clusterization pattern of water molecules in a human body, the method comprising:
   launching a healing application on a mobile device, the application configured to play an audio file;
   plugging the mobile device into a power outlet for receiving a carrier signal having a frequency of approximately 50 or 60 Hz;
   attaching a first connector to an audio outlet of the mobile device;
   selecting a type of ailment to be cured in the healing application;
   embedding an ailment-specific healing signal of between 10 KHz and 700 KHz into the carrier signal by playing an audio file corresponding to the selected ailment, so as to generate an alternating electric signal having about 1 mA of current through the connector flowing into the human body at about 1-1.5 V rms and about 1.5-1.9 V peak-to-peak;
   transmitting the alternating electric signal into the first connector and passing the alternating electric signal into the human body by placing a second connector in direct contact with a skin of the human body,
   wherein the first and second connectors are connected by a cable,
   wherein the alternating electric signal causes changes in the clusterization pattern of water molecules in the human body.

2. The method of claim 1, wherein the second connector is cylindrical.

3. The method of claim 1, wherein the second connector is oval-shaped in cross-section.

4. The method of claim 1, wherein the second connector is flat-shaped.

5. A system for changing clusterization pattern of water molecules in a human body, the system comprising:
   a mobile device with a healing application configured to play an ailment-specific audio file;
   a charger for connecting the mobile device to a power outlet for receiving a carrier signal having a frequency of approximately 50 or 60 Hz;
   a first connector in communication with an audio outlet of the mobile device;
   wherein the application is configured for selecting a type of ailment to be cured in the healing application and for embedding an ailment-specific healing signal of between 10 KHz and 700 KHz into the carrier signal to generate an alternating electric signal by playing an audio file corresponding to the selected ailment;
   wherein the first connector is configured to receive the alternating electric signal file into a second connector and the second connector is configured to pass the alternating electric signal into the human body when the second connector is configured to be placed in direct contact with a skin of the human body so as to deliver about 1 mA of current into the human body at about 1-1.5 V rms and about 1.5-1.9 V peak-to-peak,
   wherein the first and second connectors are connected by a cable to thereby cause changes in the clusterization pattern of water molecules in the human body.

6. The system of claim 5, wherein the second connector is cylindrical.

7. The system of claim 5, wherein the second connector is oval-shaped in cross-section.

8. The system of claim 5, wherein the second connector is flat-shaped.

9. The system of claim 5, wherein the second connector is configured to have an area of contact with the human body of at least 5 cm$^2$.

* * * * *